United States Patent [19]

Bruno

[11] Patent Number: 4,955,477

[45] Date of Patent: Sep. 11, 1990

[54] RECEPTACLE FOR STORAGE AND DISPOSAL OF POTENTIALLY INJURIOUS IMPLEMENTS SUCH AS USED SCALPEL BLADES, HYPODERMIC NEEDLES AND THE LIKE

[76] Inventor: John Bruno, 77-83 Second Ave., Paterson, N.J. 07514

[21] Appl. No.: 455,983

[22] Filed: Dec. 22, 1989

Related U.S. Application Data

[63] Continuation of Ser. No. 384,879, Jul. 24, 1989, abandoned, which is a continuation of Ser. No. 311,429, Feb. 14, 1989, abandoned, which is a continuation of Ser. No. 898,973, Aug. 22, 1986, abandoned, which is a continuation-in-part of Ser. No. 833,335, Feb. 15, 1986, abandoned, which is a continuation-in-part of Ser. No. 826,288, Feb. 5, 1986, abandoned.

[51] Int. Cl.$^5$ .............................................. B65D 25/00
[52] U.S. Cl. .................................. 206/366; 206/635; 220/1 T
[58] Field of Search ................... 206/366, 63.5; 220/17
[56] References Cited

U.S. PATENT DOCUMENTS

| 632,040 | 8/1899 | Braun et al. | 232/63 |
| 915,308 | 3/1909 | Rebischung | 232/57 |
| 940,727 | 11/1909 | Quinn | 232/57 |
| 948,783 | 2/1910 | Johnson | 232/15 |
| 2,527,318 | 10/1950 | Magnus | 220/338 |
| 4,121,755 | 10/1978 | Meseke et al. | 206/366 |
| 4,315,592 | 2/1982 | Smith | 206/366 |
| 4,351,434 | 9/1982 | Elisha | 206/366 |
| 4,466,538 | 8/1984 | Giannl | 206/366 |
| 4,485,918 | 12/1984 | Mayer | 206/366 |
| 4,488,643 | 12/1984 | Pepper | 206/366 |

FOREIGN PATENT DOCUMENTS

13768 6/1904 Norway ............................ 232/31

Primary Examiner—Joseph Man-Fu Moy
Attorney, Agent, or Firm—Morgan & Finnegan

[57] ABSTRACT

A receptacle for storage and disposal of potentially injurious implements, is adapted to receive implements in a compact side-by-side horizontal configuration for maximum storage capacity. Such receptacle substantially prevents implements stored therein from falling out after closure of the receptacle container which can be conveniently discarded in an appropriate disposal facility. In addition, the receptacle also prevents a person's hand from contacting such implements within the receptacle.

8 Claims, 9 Drawing Sheets

RECEPTACLE FOR STORAGE AND DISPOSAL OF POTENTIALLY INJURIOUS IMPLEMENTS SUCH AS USED SCALPEL BLADES, HYPODERMIC NEEDLES AND THE LIKE

This is a continuation of co-pending application Ser. No. 07/384,879, filed on 7/24/89; which is a continuation of 7/311,429, filed on 2/14/89; which is a continuation of 06/898,973 filed 8/22/86; which is a continuation-in-part of 06/833,335 filed 2/15/86; which is a continuation-in-part of 06/826,288 filed 2/5/86, all now abandoned.

BACKGROUND AND OBJECTS OF THE INVENTION

The present invention relates generally to receptacles, containers and the like, and, more particularly, to receptacles for safe storage and ultimate disposal of potentially injurious or contaminated implements such as used scalpel blades, hypodermic needles and like devices which pose a risk of causing infection or even disease by exposure to such implements.

With the advent of disposable medical implements such as surgical tools, hypodermic needles, scalpel blades and other sharp implements, a need has developed for a receptacle to safely store, and safely handle for disposal, such implements after use without risk of exposing people to injury, infection or disease by improper handling, until proper disposal can be made. The tragic outbreak of the highly contagious AIDS disease has dramatically highlighted the need for safer handling, storage and disposal of such implements.

In the case of disposable hypodermic needles, it had been common practice to break or cut the needles prior to discarding the needle and syringe in order to reduce the size of the overall needle/syringe device and to eliminate the sharp point from the needle to reduce the risk of injury which might otherwise result from handling. In breaking or cutting the needles, however, a substantial danger exists of accidental puncture during the breaking or cutting operation, thus exposing the holder to possible injury and, further, to possible infection or disease as a result of such puncture. In addition, any residual medication in the needle can splatter onto the person or his clothes and there is a further danger that potentially harmful fumes can be inhaled. The blades of the cutting tool also become a breeding ground for germs, bacteria and other disease-causing micro-organisms to which the unsuspecting person cutting the needle is unnecessarily exposed.

Recently, an even greater danger has been recognized in connection with the handling and dismantling of used needles and other sharp medical implements. It is now recognized that certain diseases, most notably Hepatitis B, can be transmitted by covert percutaneous—i.e., by merely contacting the contaminated needle or implement.

As a result of the foregoing dangers, the preferred current practice is to dispose of such devices intact, without dismantling them. Often, hypodermic needles are re-capped after use with the protective sheaths used during shipment from the manufacturer, in order to prevent injury while carrying the device to a suitable disposal unit. This practice itself, however, often results in puncture wounds suffered while re-capping the needle point. Because of this danger it is now recommended that needles not be re-sheathed after use.

Although certain proposals have been advanced for eliminating some of the risks involved in the handling, storage and disposal of hypodermic needles and other sharp medical implements, they generally do not overcome all of the dangers. In fact, they themselves can become the source of other problems. For example, there are several specially designed containers for storing used hypodermic needles, including some made of all plastic and some made of all cardboard, as identified, for example, in my two earlier-filed co-pending Pat. applications (application Ser. No. 513,616, filed July 14, 1983, and application Ser. No. 746,047, filed June 17, 1985 the disclosures of which are both hereby incorporated by reference herein).

Although such specially designed devices provide adequate results under certain circumstances, they do suffer certain disadvantages as explained in my aforesaid copending applications. Of particular concern is the fact that in virtually all of these containers, either the entire syringe/needle or the syringe with the needle stub is dropped vertically into the containers, thus creating a haphazard distribution of needles in the container. Such distribution usually results in an inefficiently filled container and can be the cause of possible injury to the user who may attempt to reach into the receptacle to rearrange the implements and make room for additional implements. Furthermore, the containers will likely end up in a dangerously overfilled condition wherein personnel will attempt to "stuff" more devices than can be safely handled and thereby result in a serious risk of puncture.

As set out in my aforesaid co-pending applications, the receptacles and containers disclosed therein (also sold under the mark "D.D.BOX" by D.D.Box Inc. of Paterson, N.J. and Highland Beach, Fla.) overcome virtually all of the foregoing drawbacks. However, even with the advantages achieved by my previous containers and receptacles, some hospital administrators and other medical personnel still express a desire for a self-contained, all-plastic storage/disposal container which will provide protection against injury from or contact with discarded implements and still allow horizontal drop of implements as in my previous containers and receptacle assemblies.

One all-plastic container which attempts to provide a unitary, all-plastic, horizontal drop container is sold by Frontier Plastics under the designation "Sharpsafe". Although the "Sharpsafe" device provides generally adequate results in certain applications, it does suffer some notable drawbacks. For example, although it includes a slanted-wall chute at its opening to permit horizontal deposit of used needles, it provides no means for ensuring that the needles will remain in a horizontal orientation as they fall into the container. In addition, there is no means for preventing a person either from inserting a needle in a vertical or other non-horizontal orientation or from reaching into the container so as to risk possible puncture or injury. Moreover, a person has to rely on his or her visual depth perception when looking into the opening to determine whether the container has reached a filled or overfilled condition, and, it is not difficult to try to remove implements from the container by reaching into it especially when filled or overfilled. It also involves three separate parts that are assembled by a somewhat complicated interfitting arrangement.

Accordingly, it is an object of the present invention to provide a new and improved receptacle for storage and disposal of hypodermic needles, scalpels and other sharp or pointed implements which pose a health risk by reason of injury, puncture or even mere contact (hereinafter referred to collectively as "potentially injurious implements", or simply "disposable implements"). It is another object of the present invention to provide a new and improved receptacle for storing potentially injurious implements, which is sturdy and resistant to puncture by the implements retained therein, yet permits convenient and complete disposal of the implements together with the receptacle.

It is also an object of the invention to provide a new and improved receptacle for storage and disposal of potentially injurious implements, which is adapted to receive implements in a compact side-by-side horizontal configuration for maximum storage capacity. It is another object of the invention to provide such a receptacle which substantially prevents implements stored therein from falling out after closure of the receptacle, and which provides a permanently sealable disposable container which can be conveniently discarded in an appropriate disposal facility. In addition, it is an object of the invention to provide such a receptacle which prevents a person's hand from contacting such implements within the receptacle.

It is yet a further object of the present invention to provide a new and improved receptacle for storing potentially injurious implements, which is compact, and can be conveniently mounted to any wall or other desired structure, yet can also be decorated for producing an attractive receptacle which can be installed in doctor offices, patient rooms or other hospital areas.

It is still another object of the invention to provide a new and improved receptacle for storing potentially injurious implements, which remains open and accessible for deposit of implements, yet passively prevents hand entry into the receptacle without requiring any moving parts such as a door, lid or like closure member which must be opened and closed each time it is used.

It is still a further object of the invention to provide such a receptacle which permits simply placing the potentially injurious implements at the opening of the receptacle and ensures that each implement will be deposited in a horizontal orientation into the receptacle for efficient side-by-side stacking of implements, and prevents a person from depositing such an implement in a vertical or other non-horizontal orientation. In addition, it is an object of the invention to permit such simple deposit of the implements while substantially preventing a person's hand from reaching inside the receptacle.

It is yet another object of the invention to provide such a receptacle which facilitates a person's ability to easily recognize when the receptacle has been filled to its intended capacity or has reached an overfill or dangerous overfill condition. Furthermore, it is an object of the invention to provide a small compartment which allows the receptacle to be safely overfilled with a few additional implements when, for example, there may be insufficient time to dispose of a filled receptacle and locate a fresh one.

It is yet a further object of the present invention to provide a new and improved receptacle of the foregoing type which includes mounting means adapted to provide further resistance to hand entry into the receptacle, yet still permits easy visual detection of the overfill condition.

It is also an object of the invention to provide a receptacle of the foregoing type which is adapted to permit relatively simple but secure closure of the receptacle when filled. Further, it is an object of the invention to provide such a receptacle which is adapted to permit full closure even if the receptacle has reached the overfilled or dangerously overfilled condition.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention comprises a receptacle for the deposit, storage and ultimate disposal of disposable medical implements, which includes a containment member adapted to store a plurality of implements and a top assembly securable to the containment member for forming the top portion of the receptacle. The top assembly includes an opening for receiving implements to be stored in the receptacle, a guide member depending angularly downwardly from adjacent one edge of the opening and a back-drop/stop member depending downwardly from the top member along a portion of the opposite side of the opening from the guide member, with the distal edges of the back-drop/stop member and guide member defining a slot-like gap wide enough to permit implements of predetermined size to pass in a horizontal orientation into the containment portion.

As preferably embodied, a closure member is provided for sealing the opening in the top member after the receptacle is filled. In one embodiment, the closure member can be snap-fit over the opening, preferably along a recessed shoulder formed along at least portions of the rim of the opening so that it is essentially flush with the top surface of the top member to resist prying open. In another embodiment, the closure member is pivotally mounted to the top member. The pivotal mounting may be accomplished either by a pin and recess arrangement or by a forming the closure member integrally with the top member, attached by a reduced thickness web which forms a "living hinge" attachment.

Also as preferably embodied, an edge of the top member opening and the opposite, distal, edge of the guide member have oppositely projecting jagged or serrated edging to deter hand entry into the receptacle. Further advantageously, either or both of the top and containment members include a slotted flange to allow mounting to a wall bracket which, preferably, can be locked.

According to a further preferred aspect of the invention, the mounting flange is located along the edge closest to the joinder of the sloping guide member. By such location, the guide member not only blocks visual observation of the interior of the receptacle, but also increases the difficulty for a person to attempt hand entry into the receptacle, yet it still permits readily visible recognition of an overfill condition.

As further preferably embodied, the back-drop/stop is adapted to be relatively flexible so that it will yield when subjected to a force, such as needles being urged against it when the closure member is closed against any needles that may be located at the mouth of the receptacle opening. Such flexibility may be provided either by tapering the back-drop/stop or by reducing the thickness of the back-drop/stop along its line of joinder with the top member, as by forming a weakened line of attachment.

It will be appreciated by those skilled in the art that the foregoing brief description and the following detailed description are exemplary and explanatory of the invention, but are not intended to be restrictive thereof. Thus, the accompanying drawings, referred to herein and constituting a part hereof, illustrate preferred embodiments of the invention and, together with the detailed description, serve to explain the principles of the invention.

DETAILED DESCRIPTION OF PREFERRED EMBODIMENTS

Turning now to the accompanying drawings wherein like reference characters refer to like parts throughout the various views and in the various embodiments, there is shown in FIGS. 1-6, one preferred embodiment of the receptacle (indicated generally at 10) for receiving and storing potentially injurious implements according to the present invention.

Figure 1:
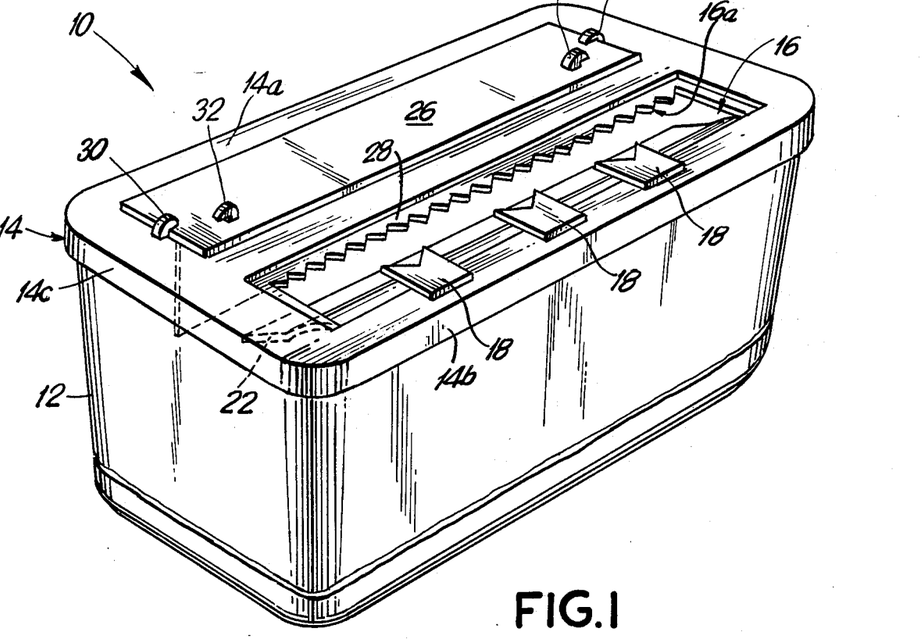
FIG. 1 is an isometric view of one preferred embodiment of a receptacle according to the present invention.

As here embodied, receptacle 10 comprises a container-like housing which, for convenience of fabrication, includes a containment member (12) which provides sufficient volume to enable storage of a desired number of implements, and a top member (14) which provides means for safely depositing the implements into the receptacle in a horizontal orientation for efficient storage in the chamber portion while preventing a person from reaching his hand into the receptacle in accordance with the present invention. It will be understood that containment member 12 is proportioned to accommodate any size implement desired and any number thereof. Since the top and containment members are advantageously made separately for ease of fabrication (e.g., by simple two-part injection molding techniques) they may preferably include any known means for securely attaching or locking them together, such as interlocking sear members (13a) formed on top member 14 and lip members (indicated at 13b in FIG. 11) formed along the top rim of containment member 12.

It will also be understood that the material and wall thickness of containment member 12 should be selected to ensure that none of the implements stored therein can damage it or cause poke-through. For example, for most commonly used thermoplastic materials, the wall thickness should be at least about 40 thousanths of an inch (0.040") thick and more preferably at least about 50 thousanths of an inch (0.050") thick. As preferably embodied, top member 14 should likewise be made of a material and wall thickness which are sufficiently strong and resilient to withstand the repeated deposit of implements and provide a secure closure of the receptacle. Advantageously, top member 14 includes a top wall 14a with two oppositely disposed downwardly extending side walls 14b and two oppositely disposed downwardly extending end walls 14c to lockably engage the containment member. It will be understood that the sear and lip engagements between top member 14 and the upper rim of containment member 12 provide a secure interlock between the two members while the continuous depending side and end walls, 14b and 14c, provide a protective skirt around the top of containment member 12 to prevent access into the receptacle along the line of joinder between these two members.

Top member 14 is adapted to receive disposable implements as large as 60 cc syringes yet prevent a person from reaching his or her hand into the receptacle to touch the implements stored therein. To this end, the top member 14 includes a generally rectangular opening 16 which is at least long and wide enough to receive the largest implement (including the flange on a syringe) desired to be stored in the receptacle. Thus, for example, for a 60cc needle and syringe opening 16 may be about 8-12 inches long and about 1 ¾-2 ½ inches wide.

Advantageously, guard tabs 18 may be formed along one or both side edges of opening 16 to allow passage of the implement while preventing access into the receptacle by a person's hand. Advantageously, there are at least two guard tabs and they are provided with sharply pointed distal edges, as indicated at 18a in FIG. 2. It will be understood that, to ensure a person's hand will not fit through opening 16 and into the receptacle, the spacing between adjacent guard tabs 18 should be about 3 ¼-4 inches or less, and, the spacing between the distal points 18a and the opposite edge of opening 16 should be no greater than about 1 ½ inches which will still allow 60cc syringes to pass through the opening. Depending on the size of implements to be deposited in the receptacle, the distance between the distal edge of guide panel 22 and the top wall 14a may be as much as about 1 ⅛" to accept 60cc syringes and the spacing between the distal edge of panel 22 and back-drop panel 24 may likewise be about 1 ⅛".

Figure 2:
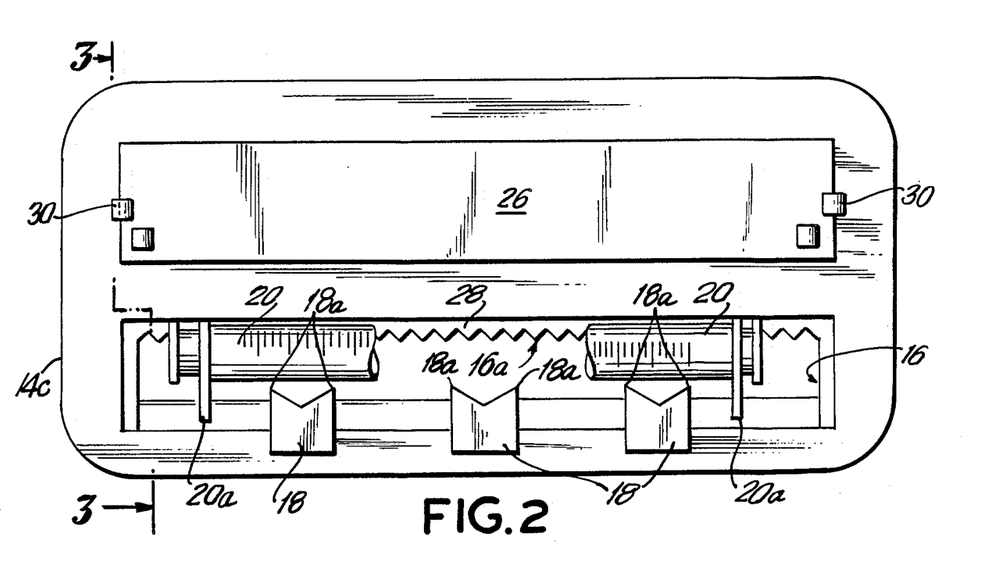
FIG. 2 is a top view of the receptacle embodiment shown in FIG. 1.

Advantageously, the edge of opening 16 opposite distal points 18a has a serrated or sharp saw-tooth edge, as indicated at 16a in FIG. 2, to further deter a person from trying to reach his or her hand through opening 16. Thus, as shown in FIG. 2, introduction of a large needle/syringe (indicated at 20) is carried out simply by laying it horizontally over opening 16, with the syringe flange (20a) located in a space between one of the guard tabs 18 and the end edge of opening 16, so it will drop through opening 16 simply by the action of gravity.

Figure 3:
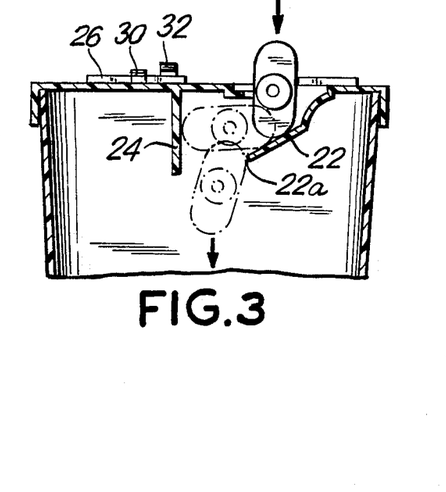
FIG. 3 is a sectional view taken along lines 3-3 of FIG. 2.
Figure 4:
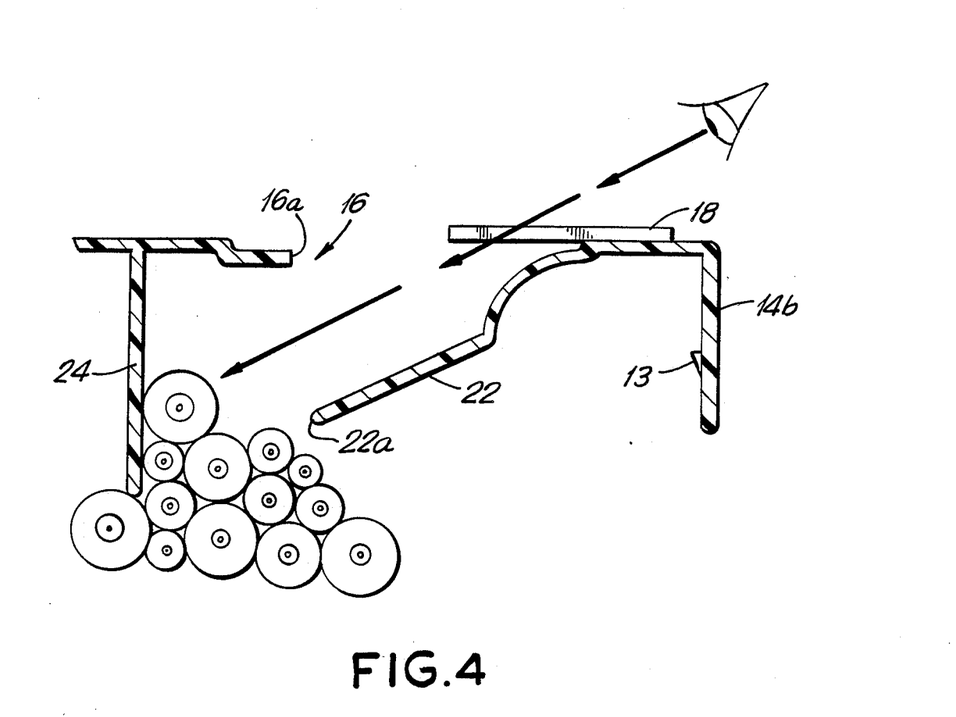
FIG. 4 is an enlarged side view similar to FIG. 3 illustrating how a person can easily inspect the receptacle to determine whether the receptacle has reached the filled or overfilled condition.
Figure 5:
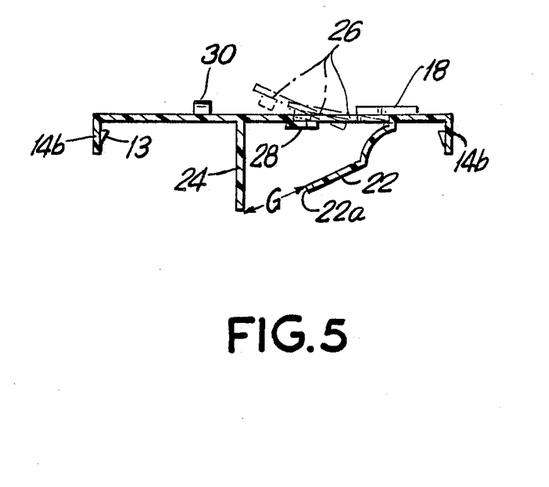
FIG. 5 is another side view similar to FIG. 4 showing the closure sequence for the embodiment of receptacle illustrated in FIG. 1.

Turning now to FIGS. 3–5 there are shown additional features according to the invention. Top member 14 advantageously includes panel-like guide member 22 extending angularly inwardly from an inward edge (here, the front inward edge) of opening 16 to guide the implements into the containment member once they are past opening 16, as will be described more fully hereinafter. Advantageously, guide panel 22 extends from the same edge as guard tabs 18 to facilitate fabrication by two-part injection molding techniques. (It will be understood by those skilled in the art that guide panel 22 may be formed with openings corresponding in shape to guard tabs 18 in order to form tabs 18 by such molding techniques.)

As further preferably embodied, the inwardly projecting distal edge (indicated at 22a) of guide panel 22 is serrated or otherwise formed with a sharp or jagged saw-tooth edge similar to edge 16a, to further deter a person from reaching into the receptacle. Jagged edge 22a may be used in addition to or instead of guard tabs 18. For ease of molding, it may be preferable to form only the oppositely projecting jagged edges 16a and 22a which, in combination with the somewhat tortuous entry path provided by members 22 and 24 (described below), should be sufficient to deter hand entry into the receptacle.

Also advantageously and as preferably embodied, top member 14 includes back-drop/stop member, here in the form of panel-like wall 24 which extends perpendicularly from top wall 14a. Back drop/stop 24 not only cooperates with guide panel 22 to ensure that implements drop into the receptacle in a horizontal orientation and that hand entry is deterred, but it also acts as a visual back drop to facilitate inspection of the interior of the receptacle to determine whether the receptacle is filled or over-filled.

Figure 6:
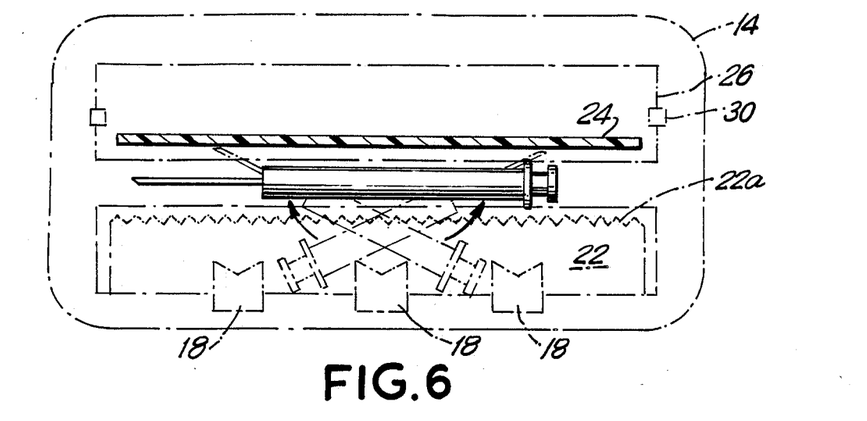
FIG. 6 is a top view of the receptacle embodiment shown in FIG. 1, showing how the invention prevents deposit of implements in a non-horizontal orientation.

In operation, once an implement is dropped through opening 16, it travels (by sliding or rolling) along guide member 22 under the influence of gravity until it reaches back-drop/stop 24. Member 24 momentarily slows/stops travel of the implement to ensure that it is aligned in a horizontal orientation and parallel to the walls of containment member 12, before it free-falls, through the slot-like gap (G) between the distal edges of members 22 and 24, into containment member 12, as illustrated in FIG. 3. In this way, the implements will land and become horizontally stacked (generally parallel to the receptacle walls) in side-by-side relation for the most-efficient packing of implements. Moreover, as illustrated by FIG. 6, it will be readily apparent that even if a person tries to introduce implements in a configuration other than a generally horizontal orientation, the implements will necessarily become re-oriented to a horizontal orientation by the co-action of their impact against guide member 22 and back-drop/stop 24. Thus, if a person tries to insert a needle/syringe at a 45° angle relative to the receptacle walls (as indicated in phantom in FIG. 6), the guide panel 22 and back-drop panel 24 will force the implement to assume the horizontal/parallel orientation described above (as indicated by the darkened implement shown in FIG. 6).

FIG. 4 illustrates how back-drop panel 24 also aids a person's visual inspection of the level of fill in the receptacle. As the receptacle is filling, the level of implements rises. However, without back-drop panel 24, a person would have to rely on his or her visual depth perception while looking through a slot or opening to determine whether a receptacle is filled, and it may be very difficult to determine whether it has reached an overfilled or a dangerously overfilled condition where no further implements should be deposited. With the back-drop panel, one can easily determine by a quick glance whether the receptacle is filled because an implement will be immediately visible against back-drop panel 24, as can be seen from the illustration in FIG. 4. Of course, it will be understood that the receptacle can be gently tapped to ensure that the implements are settled in the receptacle so that it will fill to capacity.

The combination of back-drop/stop 24 and guide member 22 are further advantageous in providing a small chamber above the containment member to receive a few additional implements, thereby allowing the receptacle to be overfilled without reaching a dangerously overfilled condition, (e.g., with sharp points immediately at, or protruding from, opening 16), and, it permits an immediately visible indication that the receptacle has reached an overfill condition. Thus, guide panel 22 acts as a guide for deposit of implements, a barrier against insertion of a person's hand, and an overfill tray to help support a few additional implements without resulting in a dangerous overfill condition.

Referring to FIG. 5, there is illustrated one embodiment of closure means according to the invention for securely closing the receptacle after it has been filled with implements and ready for disposal. As here embodied, the closure means includes an essentially flat closure panel 26 which is proportioned to fit fully over opening 16. To secure closure panel 26 in place, a recessed shoulder or shelf is formed (indicated generally at 28) at least along the side of opening 16 opposite guard tabs 18, with a comparable shoulder or shelf preferably formed along the side on which guard tabs 18 are formed. To this end and advantageously, guide panel 22 includes a curved portion adjacent its point of connection to top wall 14a so as to create a shelf or shoulder to receive one edge of closure panel 26. The curvature also facilitates sliding of the panel during the closure step.

In operation the closure panel 26 can be slidably stored adjacent opening 16 under lips formed in oppositely disposed storage lugs 30 formed on the top of top wall 14a, as illustrated in FIGS. 2 and 3. When the receptacle is filled and is ready for closure, closure panel 26 is removed from lugs 30 and moved towards opening 16 with one side edge slid under guide tabs 18 until seated in abutting relation with the opposite edge of opening 16, as indicated in full lines in FIG. 5. At the same time, the opposite side edge of closure panel 26 becomes seated on shoulder 28. Advantageously, in order to ensure secure closure of the receptacle, one or more sear-like locking tabs (indicated at 32 in FIG. 3) may be formed on bottom surface of closure panel to snap into place under the opposite end edges of opening 16.

Alternatively and advantageously, the closure panel may be pivotally mounted to top member 14 to further facilitate closure of the receptacle.

Figure 7:
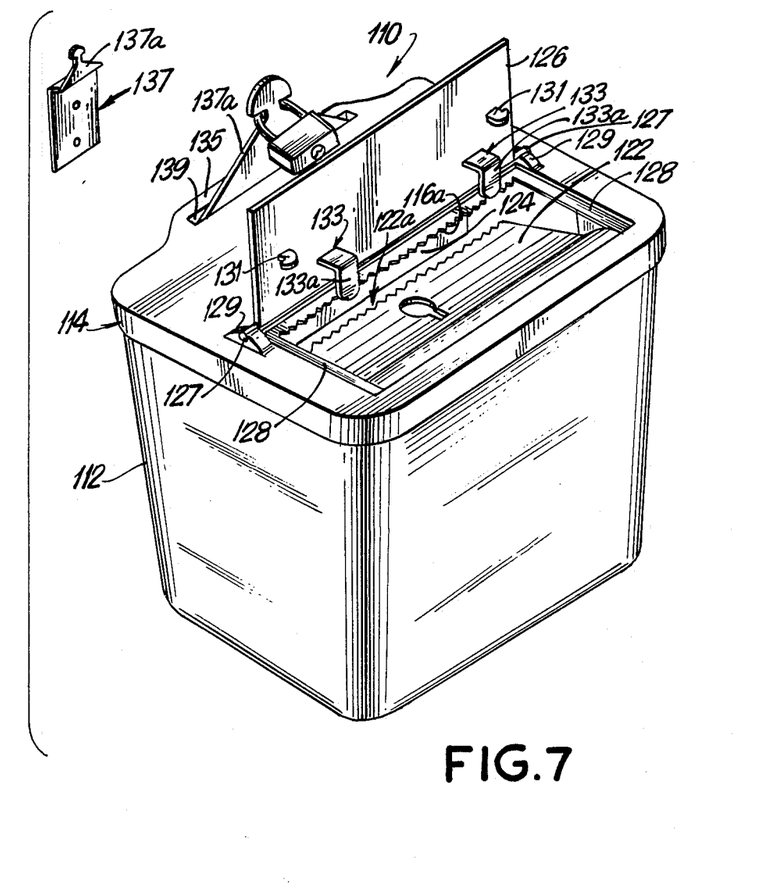
FIG. 7 is an isometric view of another preferred embodiment of a receptacle according to the present invention.

In one embodiment, shown in FIG. 7, the closure panel (indicated at 126) may be formed with a pair of rod-like projections (each designated 127) to act as the hinge pin for enabling pivotal connection of closure panel 126 to top member 114. (In essentially all other respects, top member 114 is the same as top member 14 described above with reference to FIGS. 1-6. Thus, like parts will be indicated by similar numbers, e.g., top members 14, 114 and 214, back-drop/stop 24, 124 and 224, etc.) Top member 114 includes means for receiving rod-like members 127 in order to permit pivotal movement (appoximately 180°) of closure panel 126.

As here embodied, the receiving means are in the form of lugs 129 in which are formed recesses (not numbered) which are proportioned to receive (in a snapping action) and retain rod-like members 127 in such a way as to permit pivotal movement of the closure panel.

To ensure secure closure of the receptacle after it is filled with implements, the bottom of closure panel 126 includes a pair of sear-like locking tabs (each indicated at 131) proportioned and positioned to cam over their corresponding side edges of opening 116, thereby to securely lock cover panel 126 to the top member 114. In order to prevent the cover panel from being easily pryed off at hinges 127/129, one or more L-shaped locking tabs 133 are preferably formed at the back edge of closure panel 126. The parallel legs (133a) of tabs 133 will project under the bottom surface of top member 114 when panel 126 is closed to ensure that the hinged edges cannot be pried open.

Figure 16:
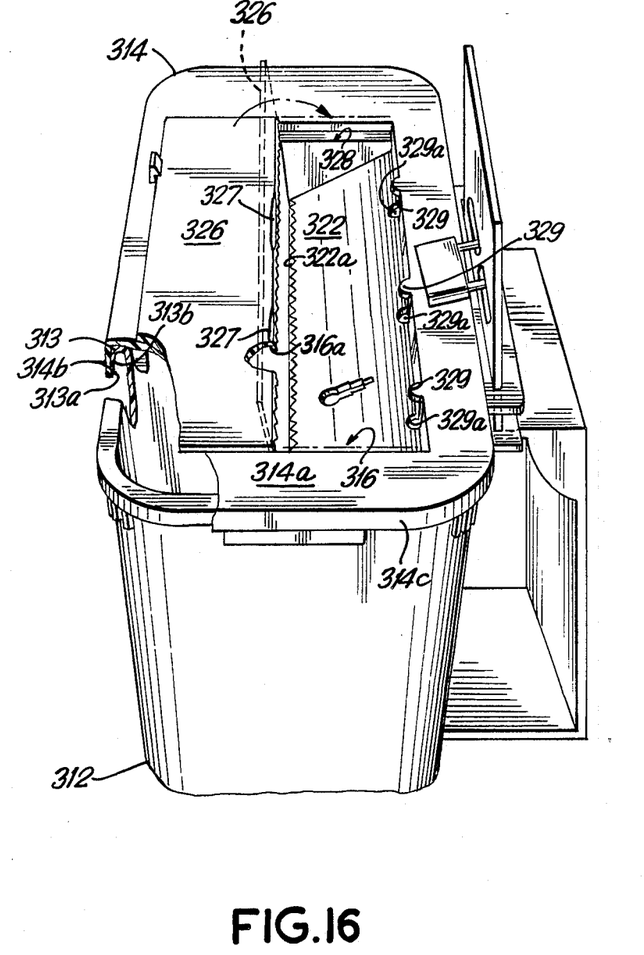
FIG. 16 is a perspective view, with partial cut-aways, of a preferred embodiment of the present invention which incorporates various preferred features of the embodiments described above with reference to FIGS. 1-15.

Also illustrated in FIG. 7 is flange 135 which may be formed along the back edge of top member 114 to facilitate lockable mounting to a wall bracket (indicated generally at 137). To this end, flange 135 is formed with a slot 139 for insertion of bracket tongue 137a which is advantageously adapted to receive a lock for securing the receptacle in place. Bracket tongue 137a may be formed with a notched segment as illustrated in FIG. 7 to receive a lock shackle, or it may simply include one or more apertures to receive the shackle (e.g., as shown in FIG. 16). It will also be understood that the containment member can also be formed with a slotted flange through which the bracket can project to support both members of the receptacle and to lock them together.

Figure 8:
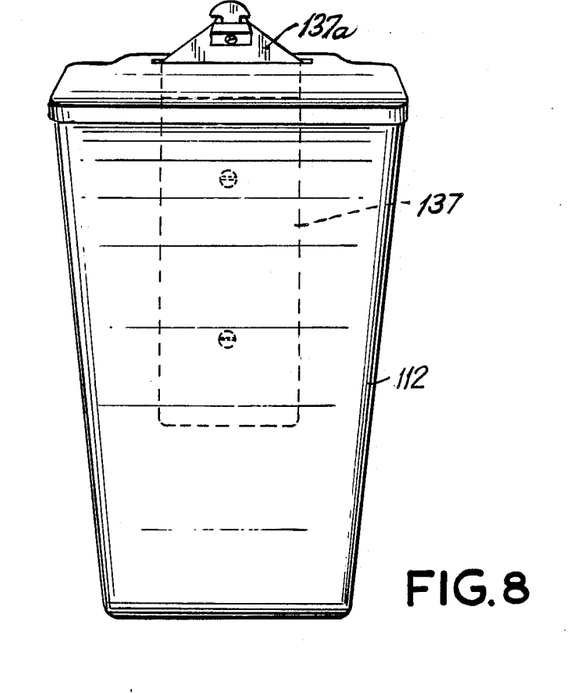
FIGS. 8 and 9 are front and side views, respectively, of a receptacle installed by wall mounting according to the present invention.
Figure 9:
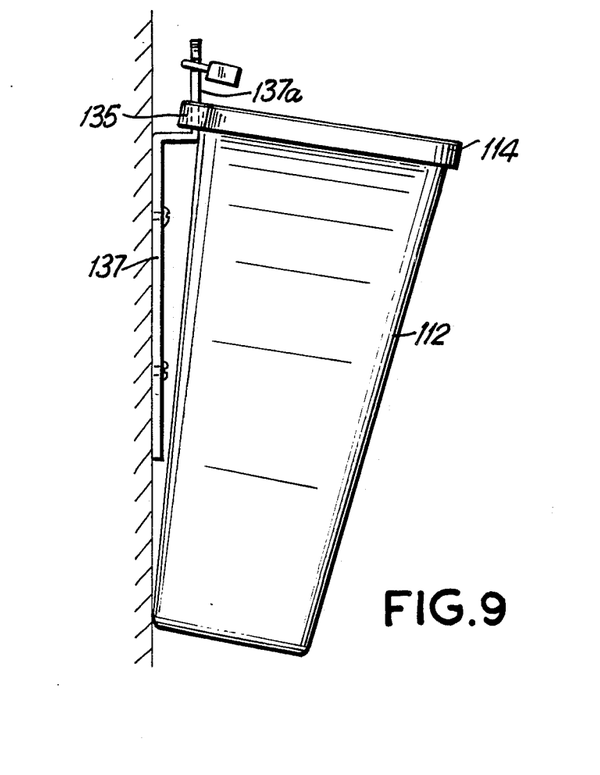

FIGS. 8 and 9 illustrate how bracket 137 can be mounted to a wall and the receptacle secured to the bracket. It will be understood that the bracket can be mounted by screws or any other convenient fasteners since they will be covered by the receptacle and thereby rendered inaccessible by unauthorized personnel. It will also be understood that the containment member can also be formed with a slotted flange through which the bracket can project to support both members of the receptacle and to lock them together.

Figure 10:
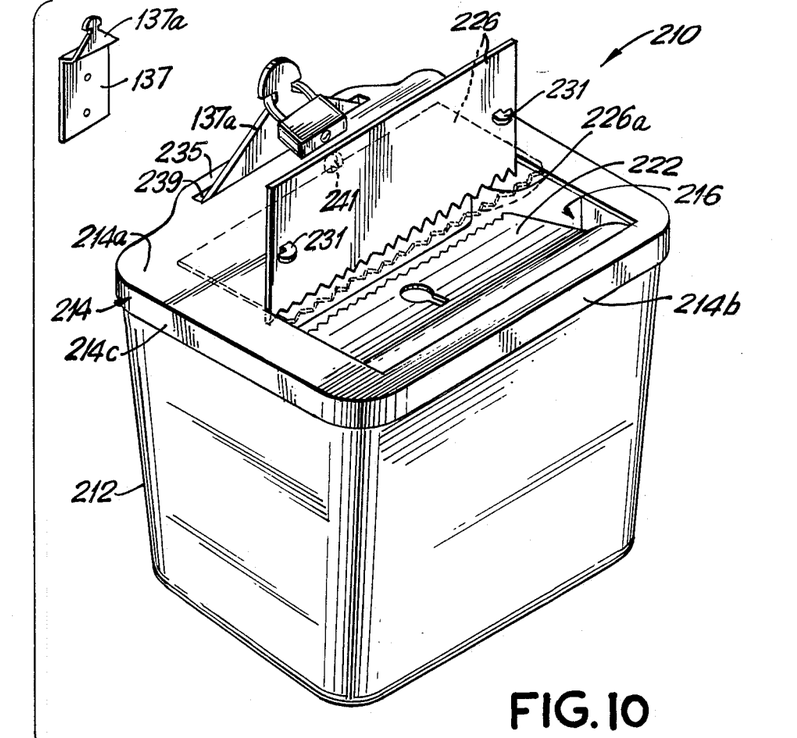
FIG. 10 is an isometric view of still another preferred embodiment of receptacle according to the present invention.
Figure 11:
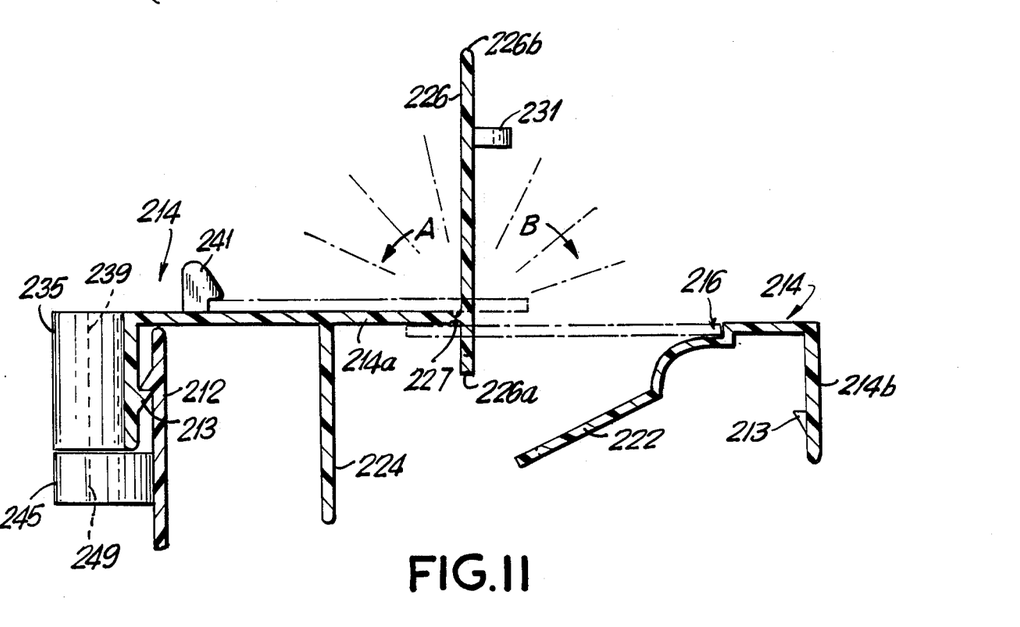
FIG. 11 is a sectional view of the top member of the embodiment illustrated in FIG. 10.

Referring now to FIGS. 10 and 11, there is shown still another preferred embodiment of receptacle according to the present invention. According to this embodiment, the closure panel (here indicated at 226) is advantageously formed integrally with top member 214, preferably by means of a "living hinge" arrangement. As here embodied, panel 226 is integrally attached along the back edge of opening 216 by reduced thickness web 227 which serves to provide a "living hinge" connection of panel 226 to the top wall 214a of top member 214. It will be understood by those skilled in the art that the foregoing integral formation and "living hinge" arrangement still permit top member 214 to be fabricated by simple two-part injection molding techniques, and, enable the overall receptacle to be made from only two separate parts which can snap-fit together for relatively easy and inexpensive fabrication and assembly.

Advantageously, top member 214 can be molded essentially in the configuration illustrated in full lines in FIG. 11 by two-part injection molding techniques. It thus includes top wall 214a with depending oppositely disposed side walls 214b and oppositely disposed end walls 214c. It further includes angularly downwardly extending guide panel 222 (with a saw-tooth or otherwise jagged distal edge substantially as described above with references to FIGS. 1-6) and downwardly projecting back-drop/stop 224. Closure panel 226 is attached by thinned web/"living hinge" 227 and may extend generally perpendicular to top wall 214a and parallel to back drop 224. In addition, the inward edge (indicated at 226a) of closure panel 226 is advantageously formed with a saw-tooth or other jagged edging. It will thus be appreciated that when closure panel 226 is folded back in the direction of arrow A and held open by latch tab 241, jagged edge 226a of the closure panel projects into opening 216 to deter a person from reaching into the receptacle, in substantially the same way as the jagged edge lip 16a disclosed above with reference to FIGS. 1-6.

After the receptacle is filled closure panel 226 can thence be rotated in the direction of arrow B until lock tabs 231 engage the opposite end edges of opening 216 to close the opening. To facilitate engagement and release of panel 226 from latch tab 241, the outward edge (indicated at 226b) may be rounded. Once the closure panel is so secured over opening 216, the implements are safely stored therein, and the receptacle can even be turned upside-down without risk that implements will fall out. Thereafter, the filled receptacle can be taken to an incinerator or other appropriate disposal unit for ultimate disposal of both the receptacle and its contents.

Advantageously, in order to facilitate molding by two-part injection molding techniques, the distal edge of the guide member may terminate at about a point directly below the opposite edge of the implement-receiving opening (i.e., the edge formed with jagged edging 16a, 116a or 216a). The back-drop/stop member may thus be recessed away from such opening edge to provide sufficient spacing to create the gap (G) between the distal edges of the guide member and the back-drop/stop member. This arrangement still provides a sufficiently tortuous path to deter hand insertion into the receptacle.

It will also be understood that a tear-drop shaped aperture may be formed in the guide members (as indicated in FIG. 7) to facilitate removal, if desired, of the needle portion from a syringe. The needle hub is simply wedged into the narrow portion of the aperture. The syringe portion is twisted until the needle is released, whereupon the needle will fall into the containment member. The area around the tear-drop aperture may be thickened to withstand repeated removal operations.

FIG. 11 also illustrates the formation of dual mounting flanges on both a top member and a containment member. As here embodied, top member 214 includes flange 235 with slot 239 formed therein to permit passage of bracket tongue 137a therethrough. Containment member 212 includes flange 245 with a similar slot 249 formed therein to likewise permit passage of bracket tongue 137a. In this way, both the top and containment members can be locked together (by use of a lock shackle passing through tongue 137a), while the weight of the receptacle will be sustained by the containment member rather than by the top member alone.

Figure 12:
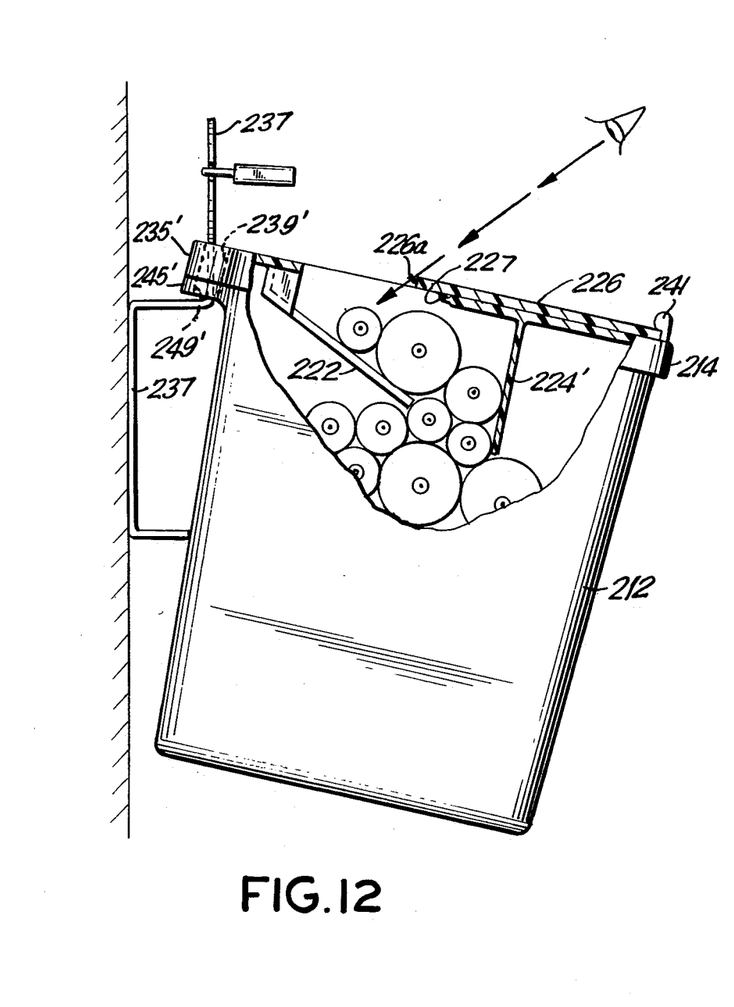
FIGS. 12 and 13 are side views of a receptacle incorporating a preferred mounting arrangement according to the Present invention.
Figure 13:
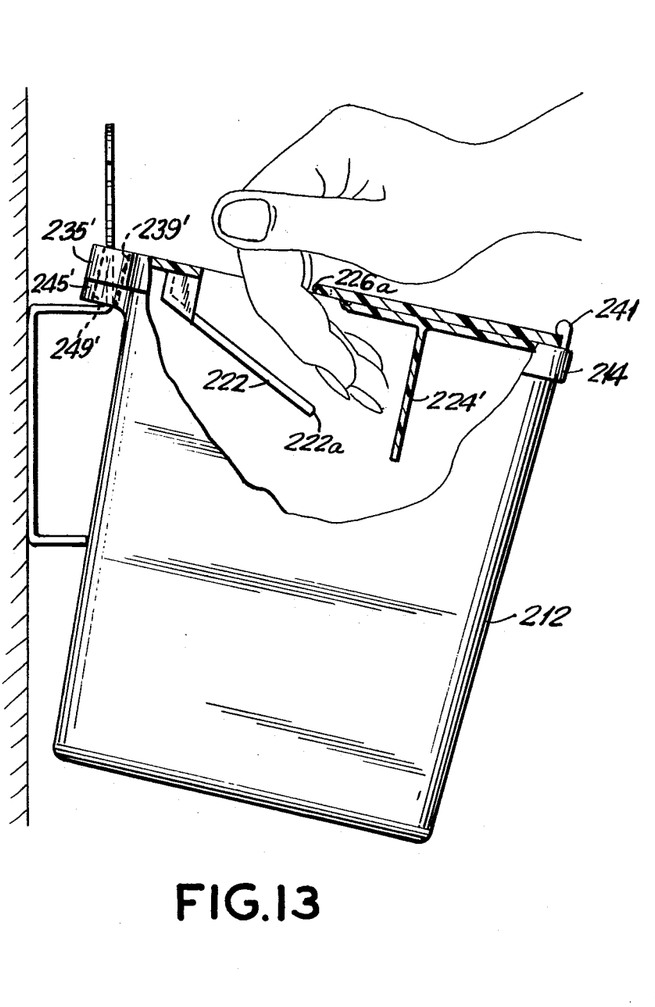

Turning to FIGS. 12 and 13, there is shown a preferred arrangement of mounting flange and bracket for mounting the receptacle to a wall. As here embodied, the slotted mounting flange (here formed both on top member 214 and on containment member 212 and indicated at 235 and 245, respectively) is advantageously formed along the receptacle edge closest to the line of attachment of guide member 222 to the top wall. The guide member thus projects away from the wall and towards a person who would be inserting used implements into the receptacle. Also advantageously, the slots 239' and 249' in the flange members are proportioned to allow the top of the receptacle to tilt slightly forward, away from the wall. Since the mounting tongue, 137a or 237a (in FIG. 13), of the wall mounting bracket, 137 or 237, will generally be spaced from the wall in order to accommodate the mounting flange, the mounting bracket will facilitate such tilting, whether or not the containment portion is tapered.

It will be understood that mounting the receptacle with the guide member projecting towards the user, the tortuous nature of the path for hand entry is even further enhanced, as indicated in FIG. 13. Moreover, since the guide member substantially blocks visual access to the contents within the containment member (except at the overfill condition), a person is, in any event, less likely to attempt hand entry into opening 216 because it means reaching into a blind opening with contaminated implements that are concealed from sight. In addition, the person's finger tips would be upside-down thereby making it difficult, if not impossible, to grasp such implements to try to withdraw them. Despite this, one can still easily observe an overfill condition because the disposable instruments will be directly visible against the guide panel 222, as indicated in FIG.-12.

Figure 14:
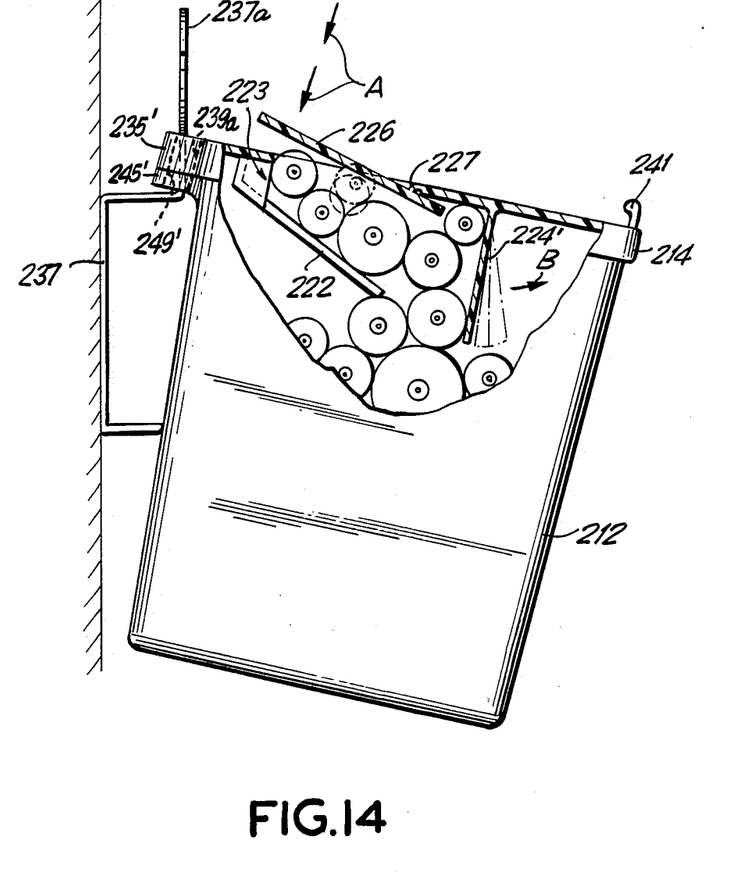
FIG. 14 is a view similar to FIG. 12 illustrating a preferred embodiment of back-drop/stop according to the present invention.

Turning now to FIG. 14, there illustrated a further aspect of the invention. According to this feature, the back-drop/stop member (indicated at 224') is adapted to be somewhat flexible. By providing such flexibility, it will be understood that secure closure of the receptacle can be achieved even if the receptacle is overfilled to such a point that discarded implements protrude beyond the top surface of top member 214. Accordingly, as closure panel 226 is rotated into its final closure position, it will urge any discarded implements in the overfill chamber (indicated generally at 223 and made up of the space bounded by the guide member, the back-drop/stop member and the top wall of the top member) back into the containment chamber, as illustrated by arrows A in FIG. 14. Because back-drop/stop 224' has flexibility, it will move forward to accommodate the implements in the overfill chamber, as indicated by arrow B in FIG. 14.

Thus, even if the receptacle reaches a dangerously overfilled condition, the receptacle can still be safely closed and secured for ultimate disposal. It will also be understood that even though there may be a small unfilled volume in the containment member because of the presence of the guide and back-drop/stop members, the minimal amount of lost storage space is far outweighed by the advantages achieved by the invention, particularly the deterence against hand entry, the side-by-side stacking of implements and the ability to securely and safely close the receptacle even when dangerously overfilled without contacting any of the implements in the overfill chamber.

In one embodiment of flexible back-drop/stop, the actual back-drop/stop member may be formed in a generally tapered configuration. Thus, it becomes thinner and more flexible towards its inwardly projecting distal edge. In another embodiment, the back-drop/stop member may be of substantially uniform thickness, but is secured to the top member through a weakened line of attachment, to form a hinge-like attachment.

Figure 15A:
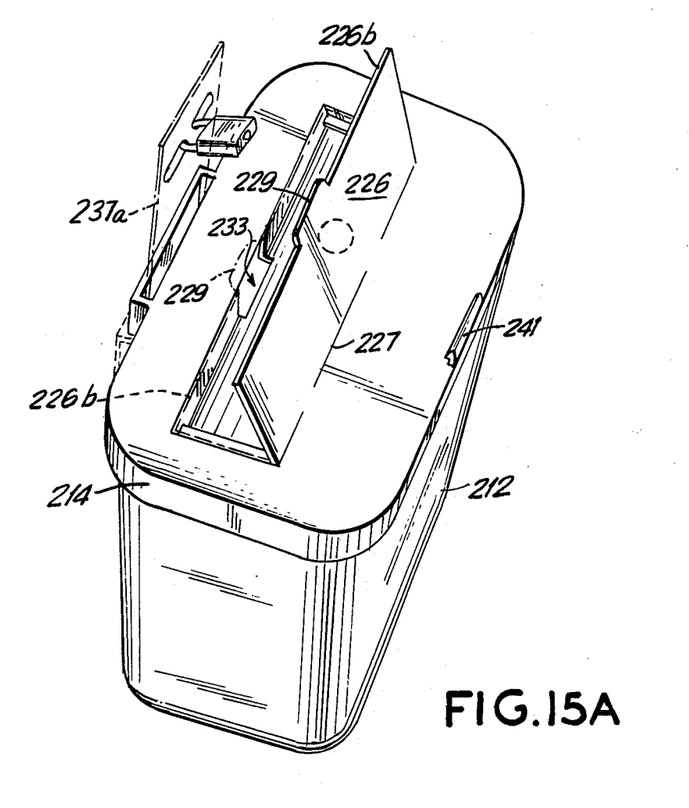
FIG. 15A and 15B illustrate, respectively, a preferred closure means and method of closure for the closure member of the receptacle according to the present invention.
Figure 15B:
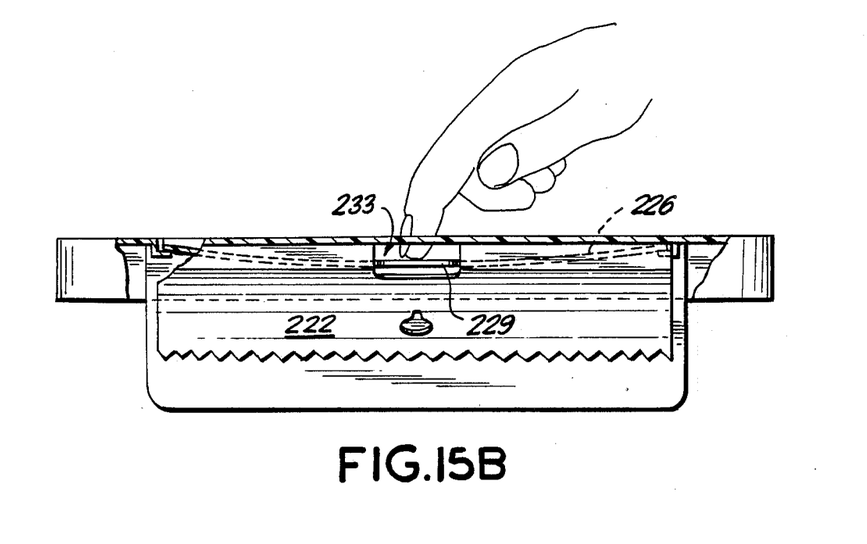

Turning now to FIGS. 15A and 15B, there is shown an alternate preferred embodiment of closure securing means according to the present invention which can be used instead of forming tabs 231 on the bottom of closure panel of 226. As here embodied, closure panel 226 includes locking tab-like Projection 229 extending from its distal edge 226b. An opening, indicated at 233, is formed in the opposite portion of guide member 222. The opening 233 is positioned so as to be in correspondence with locking tab 229 on the closure member 226 which, in turn, also corresponds to the holding lug 241 to retain the top member in an open configuration.

In operation, a user releases closure panel 229 from retaining lug 241, then begins to close it substantially as described above. As the panel reaches its fully closed position, the user can simply push down in the area designated 237, causing panel 226 to bend slightly or assume a bowed configuration, to allow the locking tab 229 to snap into opening 233. Once tab 229 is received in opening 233, the receptacle is permanently secured for ultimate disposal.

Referring now to FIG. 16, there is shown a preferred embodiment of a receptacle according to the present invention, which incorporates various preferred features of the embodiments disclosed above with reference to FIGS. 1-15. This embodiment is particularly advantageous in that it incorporates features and advantages of the present invention in a durable structure capable of relatively inexpensive fabrication by simple two part injection molding techniques.

As here embodied, the receptacle includes container member 312 which is similar to containers 12, 112 and 212 described above and includes a reinforced rim portion (indicated at 313). Rim 313 serves both to rigidify the open top of the container and to provide a downardly facing lip (indicated at 313b) which engages sear members 313a formed on the top member 314 for securing top member 314 to container 312. As in the foregoing embodiments, top member 314 includes downwardly projecting side and end walls (314b and 314c) which provide a protective skirt surrounding the top of container 312 (when interlocked together as shown in one of the broken away segments in FIG. 16) to prevent access into the container.

Top member 314 is substantially the same as top members 14, 114 and 214 described above. Guide member 322 is substantially planer in configuration and need not include any curved portions. The distal free end of guide panel 322 includes serrations or jagged teeth 322a, substantially as described above. In addition, the opposite edge of the opening (316) is also formed with serations or jagged teeth (316a) here shown projecting downardly into receptacle container 312 (as best seen in the other broken away segment in FIG. 16). Thus, as is readily apparent from the previously disclosed embodiments, jagged teeth 316a formed on the edge of opening 316 (and on the distal edge of panel 322 if desired) can be oriented in any direction in order to, e.g., facilitate fabrication (preferably by two-part molding techniques) while serving as a physical deterrent to hand insertion through opening 316. For example, top member 314 can be molded with closure panel 326 extending vertically upwardly (as shown in phantom) while the teeth 316a extend vertically downwardly in generally the same plane as panel 326 except that they are formed directly on the horizontal portion (314a) of top member 314 rather than projecting directly from the rear edge of panel 326.

The locking mechanism for closure panel 326 here includes one or more tabs (each indicated at 329) projecting outwardly from the near edge of opening 316 (i.e. the edge from which panel 322 projects) to engage the distal edge of closure panel 326, rather than forming a closure tab on the closure panel itself as shown at 229 in FIGS. 15. As here embodied, there are three such tabs which can be easily formed by two-part injection molding techniques. To facilitate such molding, it may be necessary to leave openings 329a in the wall portion formed at the junction of panel 322 and top member 314 of the opposite edge. Shoulders 328 are also provided along opposite sides of opening 316 to help support closure panel 326 when finally closed. Thus, once the container has been filled to capacity, panel 326 is released from hold-down tabs 341 and rotated 180° until it abuts the tops of tabs 329 (as indicated by the arrow in FIG. 16). By pressing panel 326 on opposite sides of each tab 329, the panel will snap under the tabs for secure closure.

Also as here embodied, the living hinge joinder between top 314 and closure panel 326 need not extend completely along the intersection of closure panel 326 and with member 314. Rather, it may be formed by one or more segments as is evident from the presence of slit-like voids 327 which result between the hinge segments. In that event, it may be preferable to form a hinge segment generally opposite as many locking tabs 329 as possible (preferably, all) to help ensure that the closure panel 326 cannot be pried open once it is closed and locked under the tabs 329.

Back-stop/wall 324 is tapered, as described above, for flexibility and for ease of molding. (If desired, serrations or jagged teeth could be formed on the back-stop/wall). As described above with reference to the foregoing embodiments, the combination of the back-stop/wall and guide panel provides wall means which enable a person to readily observe when the container is reaching the filled condition. This results from the visual contrast of implements immediately against the background of the back-stop/wall or guide panel. Thus, it will be readily appreciated by those skilled in the art that should a disposal receptacle be desired which need only provide means for facilitating recognition of an almost filled condition, one or more wall segments can be provided adjacent the opening so as to depend at any angle (e.g. 90°) from the interior surface of in the top member. Such wall means thus enable ready recognition of a filled condition from any direction of observation.

It will be appreciated by those skilled in the art that the present invention in its broader aspects is not limited to the particular embodiments shown and described herein, and that variations may be made which are within the scope of the accompanying claims without departing from the principle of the invention and without sacrificing its chief advantages.

What is claimed is:

1. A self-contained receptacle for safely storing potentially dangerous implements such as hypodermic needles, scalpel blades and the like, comprising:

a containment member proportioned to retain a plurality of implements; and a top member adapted to be attached to said containment member, said top member including an opening proportioned to receive a desired size of implements, a guide member extending generally angularly downwardly into said receptacle from said top member generally along one edge of said opening and a back-drop/stop member extending downwardly from said top member adjacent the side of said opening opposite the side adjacent to which said guide member is mounted, said back-drop/stop and guide members having distal edges which form a slot-like gap for allowing implements to drop into said receptacle, said back-drop/stop member including jagged edging facing said guide member, and said back-drop/stop member and said guide member being positioned and proportioned relative to each other to cause at least a momentary slowing of travel of implements along said guide member to ensure that each implement assumes a generally horizontal orientation before actually dropping into said containment member such that implements inserted through said opening are aligned in a generally horizontal orientation by cooperation between said guide and back-drop/stop members at said slot-like gap, thereafter to drop into said containment member for side-by-side stacking with other implements deposited therein and said jagged edging helping to deter hand entry into said receptacle.

2. A receptacle according to claim 1 wherein said containment member includes a downwardly projecting lip for engaging sear means on said top member to securely lock said top and containment members together.

3. A self-contained receptacle for safely storing potentially dangerous implements such as hypodermic needles, scalpel blades and the like, comprising:

a containment member proportioned to retain a plurality of implements; and a top member adapted to be attached to said containment member, said top member including an opening proportioned to receive a desired size of implements, a guide member extending generally angularly downwardly into said receptacle from said top member generally along one edge of said opening and a back-drop/stop member extending downwardly from said top member adjacent the side of said opening opposite the side adjacent to which said guide member is mounted, said back-drop/stop and guide members having distal edges which form a slot-like gap for allowing implements to drop into said receptacle, said back-drop/stop member including jagged edging facing said guide member, said back-drop/stop member and said guide member being positioned and proportioned relative to each other to cause at least a momentary slowing of travel of implements along said guide member to ensure that each implement assumes a generally horizontal orientation before actually dropping into said containment member, said top member including a closure member to seal said top member once said receptacle is filled with implements and tab means at said opening for locking said closure member by a generally snap-fitting action such that implements inserted through said opening are aligned in a generally horizontal orientation by cooperation between said guide and back-drop/stop members at said slot-like gap, thereafter to drop into said containment member for side-by-side stacking with other implements deposited therein and said closure member can be secured closed over said opening once the receptacle is filled.

4. A receptacle according to claim 3, wherein said closure member is integrally mounted to said top member by a reduced thickness web member which forms a living hinge therebetween.

5. A receptacle according to claim 4, wherein said top member includes jagged edging at said opening generally adjacent said living hinge.

6. A receptacle according to claim 5, wherein said jagged edging projects inwardly of said receptacle.

7. A receptacle for safely storing potentially dangerous implements such as hypodermic needles, scalpel blades and the like, comprising:

a containment member proportioned to retain a plurality of implements; and a top member adapted to be attached to said containment member said top member having an opening proportioned to receive a desired size of implements and wall means extending downwardly from said top member from its interior surface generally adjacent said opening, said top member further including a guide member extending generally angularly downwardly into said receptacle from said top member generally along an edge of said opening generally opposite at least a portion of said wall means so as to form a slot-like gap for allowing implements to drop into said receptacle, said wall means and said guide member being positioned and proportioned relative to each other to cause at least a momentary slowing of travel of implements along said guide member to ensure that each implement assumes a generally horizontal orientation before actually dropping into said containment member to ensure that implements inserted through said opening are aligned in a generally horizontal orientation by cooperation between said guide member and said wall means at said slot-like gap, such that as said receptacle is filled with implements, a person can readily observe that the receptacle is reaching a filled condition by visual contrast of implements against said wall means.

8. A receptacle according to claim 7 wherein said wall means generally surrounds said opening in said top member.

* * * * *